(12) United States Patent
Fogg

(10) Patent No.: US 10,716,486 B1
(45) Date of Patent: Jul. 21, 2020

(54) SYSTEM AND METHOD TO ESTIMATE A SIGNAL HIDDEN WITHIN A COMPOSITE WAVEFORM

(71) Applicant: Harold T. Fogg, Aurora, CO (US)

(72) Inventor: Harold T. Fogg, Aurora, CO (US)

( * ) Notice: Subject to any disclaimer, the term of this patent is extended or adjusted under 35 U.S.C. 154(b) by 86 days.

(21) Appl. No.: 16/227,014

(22) Filed: Dec. 20, 2018

Related U.S. Application Data

(62) Division of application No. 15/194,762, filed on Jun. 28, 2016, now Pat. No. 10,194,822.

(51) Int. Cl.
*A61B 5/04* (2006.01)
*A61B 5/0472* (2006.01)
*A61B 5/0468* (2006.01)

(52) U.S. Cl.
CPC ........ *A61B 5/0472* (2013.01); *A61B 5/04012* (2013.01); *A61B 5/0468* (2013.01)

(58) Field of Classification Search
None
See application file for complete search history.

(56) References Cited

U.S. PATENT DOCUMENTS

| 9,597,001 B2 | 3/2017 | Zigel et al. |
| 2015/0133808 A1 | 5/2015 | Lee et al. |

*Primary Examiner* — Brian T Gedeon
(74) *Attorney, Agent, or Firm* — Shifrin Patent Law; Dan Shifrin

(57) ABSTRACT

A system is provided for isolating the value of a signal hidden within a composite electrical signal. The system comprises an input, a processor, and a memory configured to store instructions executable by the processor. The instructions cause the processor to estimate that portion of a received composite electrical signal that represents a hidden signal by subtracting a known first signal from the composite signal.

10 Claims, 12 Drawing Sheets

| | | M₁ | M₂ | M₃ | M₄ | M₅ | M₆ | M₇ | M₈ | M₉ | M₁₀ | M₁₁ | M₁₂ | M₁₃ | M₁₄ | M₁₅ | M₁₆ | M₁₇ | M₁₈ |
|---|---|---|---|---|---|---|---|---|---|---|---|---|---|---|---|---|---|---|---|
| | | 0 | $P_1$ | $P_2$ | $P_3$ | $Q_1$ | $Q_2$ | $Q_3, R_1$ | $R_2$ | $R_3, S_1$ | $S_2$ | $S_3$ | $T_1$ | $T_2$ | $T_3$ | $U_1$ | $U_2$ | $U_3$ | |
| M₁ | 0 | 0 | - | - | - | - | - | - | - | - | - | - | - | - | - | - | - | - | , |
| M₂ | $P_1$ | $P_1-0$ | 0 | - | - | - | - | - | - | - | - | - | - | - | - | - | - | - | , |
| M₃ | $P_2$ | $P_2-0$ | $P_2-P_1$ | 0 | - | - | - | - | - | - | - | - | - | - | - | - | - | - | , |
| M₄ | $P_3$ | $P_3$ | $P_3-P_1$ | $P_3-P_2$ | 0 | - | - | - | - | - | - | - | - | - | - | - | - | - | , |
| M₅ | $Q_1$ | | | | | 0 | - | - | - | - | - | - | - | - | - | - | - | - | , |
| M₆ | $Q_2$ | | | | | | 0 | - | - | - | - | - | - | - | - | - | - | - | , |
| M₇ | $Q_3, R_1$ | | | | $Q_3-P_3$ | | | 0 | - | - | - | - | - | - | - | - | - | - | , |
| M₈ | $R_2$ | | | | | | | | 0 | - | - | - | - | - | - | - | - | - | , |
| M₉ | $R_3, S_1$ | | | | | | | $R_3-R_1$ | | 0 | - | - | - | - | - | - | - | - | , |
| M₁₀ | $S_2$ | | | | | | | | | | 0 | - | - | - | - | - | - | - | , |
| M₁₁ | $S_3$ | | | | | $Q_1-S_3$ | | | | | | 0 | - | - | - | - | - | - | , |
| M₁₂ | $T_1$ | | $T_1-P_1$ | | | $T_1-Q_1$ | | | $T_1-R_2$ | | | $T_1-S_3$ | 0 | - | - | - | - | - | , |
| M₁₃ | $T_2$ | | | | | | | | | | | | | 0 | - | - | - | - | , |
| M₁₄ | $T_3$ | | | | | | | | | | | | $T_3-T_1$ | | 0 | - | - | - | , |
| M₁₅ | $U_1$ | | | | $U_1-P_3$ | | | | | | | | | | | 0 | - | - | , |
| M₁₆ | $U_2$ | | | | | | | | | | | | | | | | 0 | - | , |
| M₁₇ | $U_3$ | | | | | | | | | | | | | | | $U_1-U_3$ | | 0 | , |
| M₁₈ | | | | | | | | | | | | | | | | | | 0 | , |

FIG. 5

| | X-coordinate |
|---|---|
| M₁ | 0 |
| M₂ | P₁ |
| M₃ | P₂ |
| M₄ | P₃ |
| M₅ | Q₁ |
| M₆ | Q₂ |
| M₇ | Q₃ |
| M₈ | R₂ |
| M₉ | R₃ |
| M₁₀ | S₂ |
| M₁₁ | S₃ |
| M₁₂ | T₁ |
| M₁₃ | T₂ |
| M₁₄ | T₃ |
| M₁₅ | U₁ |
| M₁₆ | U₂ |
| M₁₇ | U₃ |
| M₁₈ | |

FIG. 6

| | Amplitude |
|---|---|
| M₁ | 0 |
| M₂ | P₁ 0 |
| M₃ | P₂ |
| M₄ | P₃ |
| M₅ | Q₁ |
| M₆ | Q₂ |
| M₇ | Q₃ |
| M₈ | R₂ |
| M₉ | R₃ |
| M₁₀ | S₂ |
| M₁₁ | S₃ |
| M₁₂ | T₁ |
| M₁₃ | T₂ |
| M₁₄ | T₃ |
| M₁₅ | U₁ |
| M₁₆ | U₂ 0 |
| M₁₇ | U₃ 0 |
| M₁₈ | |

FIG. 7

| | | Interpolation Method |
|---|---|---|
| M₁ | 0 | |
| M₂ | P₁ | |
| M₃ | P₂ | |
| M₄ | P₃ | |
| M₅ | Q₁ | |
| M₆ | Q₂ | |
| M₇ | Q₃, R₁ | |
| M₈ | R₂ | |
| M₉ | R₃, S₁ | |
| M₁₀ | S₂ | |
| M₁₁ | S₃ | |
| M₁₂ | T₁ | |
| M₁₃ | T₂ | |
| M₁₄ | T₃ | |
| M₁₅ | U₁ | |
| M₁₆ | U₂ | |
| M₁₇ | U₃ | |
| M₁₈ | | |

FIG. 8

SYSTEM AND METHOD TO ESTIMATE A SIGNAL HIDDEN WITHIN A COMPOSITE WAVEFORM

RELATED APPLICATION DATA

The present application is a divisional application of commonly-owned and co-pending U.S. patent application Ser. No. 15/194,762 entitled SYSTEM AND METHOD TO ISOLATE AND DISPLAY WAVEFORM COMPONENTS FROM A COMPOSITE WAVEFORM and filed on Jun. 28, 2016. The present application is related to the following commonly-owned U.S. Provisional Application Ser. No. 62/186,017, entitled METHOD AND SYSTEM TO ISOLATE AND DISPLAY ESTIMATED EKG WAVES and filed Jun. 29, 2015, which application is related to and claims the benefit of the following commonly-owned U.S. Provisional Applications: Ser. No. 62/082,297, entitled PHYSIOLOGICAL ELECTRICAL SIGNAL SIMULATOR and filed on Nov. 15, 2014, and Ser. No. 62/111,500, entitled SYSTEM FOR GENERATING CARDIAC WAVEFORMS and filed on Feb. 3, 2015, which applications are incorporated herein by reference in their entireties. The present invention is also related to the following commonly-owned U.S. Pat. No. 9,489,345, entitled SYSTEM AND METHOD FOR PROVIDING PRODUCTS AND LOCATIONS, and U.S. Pat. No. 10,140,316, entitled SYSTEM AND METHOD FOR SEARCHING, WRITING, EDITING, AND PUBLISHING WAVEFORM SHAPE INFORMATION, which and patents are incorporated by reference in their entirety.

TECHNICAL FIELD

The present invention relates generally to an apparatus and method for isolating estimated waveform components from composite waveforms.

BACKGROUND ART

Electrocardiograph (EKG) monitors are important, and non-invasive, diagnostic medical tools. An EKG waveform is a representation of some of the electrical activity produced by a beating heart during a period of time. Two or more electrodes are placed at various location on a patient's skin and connected to an EKG monitor. Electrical signals are generated in the heart. The signals are detected on the skin by the electrodes and received by the EKG monitor. The machine amplifies and processes the signals and converts them into a representation of the heart's activity, which may be analyzed and displayed as traces on a screen, printed onto paper, or both.

It is not the intent of this discussion to provide a detailed explanation of cardiology and the analysis of EKG traces. However, a general summary is useful for background purposes. FIG. 1 is an example of a strip chart of electrical signals from a 12-lead EKG monitor connected to a patient with a normal heart. FIG. 2 identifies individual waves, intervals, and segments. While there may be some confusion or ambiguity about the labeling of different "sections" of an EKG wave, for purposes of this application an "interval" contains one or more individual wave and a "segment" connects the end of one individual wave with the beginning of the next wave. Beginning from the left side of the chart in FIG. 2, the individual waves are: the P wave, the Q wave, the R wave, the S wave, the T wave, and the U wave (which may be overlapped and hidden by the T wave and the next P wave).

Beginning again from the left side of the chart in FIG. 2, the intervals are:
 a. the PR interval, from the start of the P wave to the beginning of the QRS interval;
 b. the PQ interval, which if used, is the same as the PR interval when the Q wave is present;
 c. the QRS interval (also known as the QRS complex), which extends from the beginning of the Q wave to the end of the S wave;
 d. the ST interval, extends from the end of the S wave to the beginning of the T wave; and
 e. the QT interval, is measured from the beginning of the QRS interval to the end of the T wave; and
 f. the RR interval, extends from the peak of one R wave of one beat to the peak of the next R wave of the next beat.

The segments are:
 a. PR segment, extends from the end of the P wave to the beginning of the Q wave;
 b. ST segment, extends from the end of the S wave to the beginning of the T wave; and
 c. TU segment, extends from the end of the T wave to the beginning of the U wave.

FIG. 3 identifies the activity of the heart muscles during each of three major phases of a beat:
 a. the P wave represents atrial depolarization;
 b. the QRS interval represents ventricular depolarization; and
 c. the T wave represents ventricular repolarization.

The wave representing atrial repolarization typically occurs between the end of the P wave and the beginning of the T wave, but is typically hidden by ventricular activity.

Many composite waveforms are interpreted or analyzed on the basis of received signals that are conditioned by a variety of processes to enhance the signal before the interpretation process begins. The conditioning process commonly includes amplification and filtering to remove from the received signal parts of the signal that are believed to not be useful for the purpose of the interpretation. One example of such a process is the interpretation of electrocardiograph (EKG) waveforms provided from EKG machines. An EKG waveform is a representation of some of the electrical activity produced by a beating heart during a period of time. The signals are detected by electrodes and received by the EKG machine, which processes the signals and converts them into a representation of the heart's activity.

It is not the intent of this discussion to provide a detailed explanation of cardiology and the analysis of EKG traces. However, it will be helpful to understand the relationship between PQRST notation and the related cardiac activity of atrial depolarization, atrial repolarization, ventricular depolarization, and ventricular repolarization. Generally, the P wave represents atrial depolarization, the QRS complex represents ventricular depolarization, and the T wave represents ventricular repolarization. Atrial repolarization (Ta wave) occurs during a time period beginning after the P wave and ending about the beginning of the T wave. The Ta is not often identified and is considered to be hidden by ventricular depolarization, which usually is much larger and occurs during about the same time period. The name Ta wave has been given to atrial repolarization activity even though its only obvious relation with the T wave seems to be that both represent repolarization. The subscript "a" is used to help avoid confusion with the T wave. It is known that atrial repolarization may influence an incorrect interpretation of the signal between the QRS complex and the T wave.

The problem of finding a Ta wave in a received EKG is somewhat like a sculptor's problem of finding an elephant in a block of stone. A problem reported to have been solved by skilled artists who say they simply remove everything that doesn't look like an elephant. Of course the problem of finding a Ta wave is different in at least two ways. On one hand, the problem is more complicated because one doesn't know what the hidden wave looks like, and the removed material must still be explained.

On the other hand, our material is more forgiving of mistakes and better suited to experimentation, analysis, automation, and inventive concepts.

SUMMARY OF THE INVENTION

An embodiment of the present invention provides a system for isolating a hidden waveform representing hidden information from a composite waveform. The system comprises: a processor; a memory configured to store instructions executable by the processor to cause the processor to estimate that portion of a received composite waveform that represents a first signal source and generate a waveform that represents an estimated first signal source; and a comparator. The comparator comprises: a first input coupled to receive the composite waveform and a second input coupled to receive the generated waveform from the processor. The comparator is configured to subtract the generated waveform from the composite waveform and output a resulting estimated hidden waveform, representing the hidden information.

Other embodiments provide a system for isolating a waveform representing atrial activity from an EKG waveform, comprising: a system input configured to receive an EKG waveform; a processor configured to receive the EKG waveform from the system input; a comparator having a first input coupled to receive the EKG waveform from the system input and a second input coupled to an output of the processor; and a memory configured to store instructions executable by the processor to cause the processor to: determine that portion of the EKG waveform that represents ventricular activity; and output the waveform that represents the ventricular activity to the second input of the comparator. The comparator is configured to subtract the estimated ventricular activity from the full EKG waveform and output the resulting waveform, representing atrial depolarization and estimated atrial repolarization.

Other embodiments provide a system for isolating a waveform representing atrial activity from an EKG waveform, comprising: a system input configured to receive a first waveform that represents an EKG waveform; a processor configured to receive the first waveform from the system input; a comparator having a first input coupled to receive the first waveform from the system input and a second input coupled to an output of the processor; and a memory configured to store instructions executable by the processor to cause the processor to: determine a second waveform that represents estimated ventricular depolarization and output the second waveform to the second input of the comparator. The comparator is configured to subtract the second waveform from the first waveform and output a third waveform, the third waveform representing atrial depolarization and estimated atrial repolarization.

Another embodiment provides a method of estimating hidden information in a composite waveform

BRIEF DESCRIPTION OF THE DRAWINGS

FIG. 5 illustrates a TABLE that may be used to enter information to specify the location of break points when constructing a representation of a heart beat waveform;

FIG. 6 illustrates another TABLE that may be used to enter information to specify the location of break points when constructing a representation of a heart beat waveform;

FIG. 7 illustrates another TABLE that may be used to enter information to specify the location of break points when constructing a representation of a heart beat waveform;

FIG. 8 illustrates still another TABLE that may be used to enter information to specify the location of break points when constructing a representation of a heart beat waveform;

DETAILED DESCRIPTION OF THE PREFERRED EMBODIMENT

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention.

Figure 1:
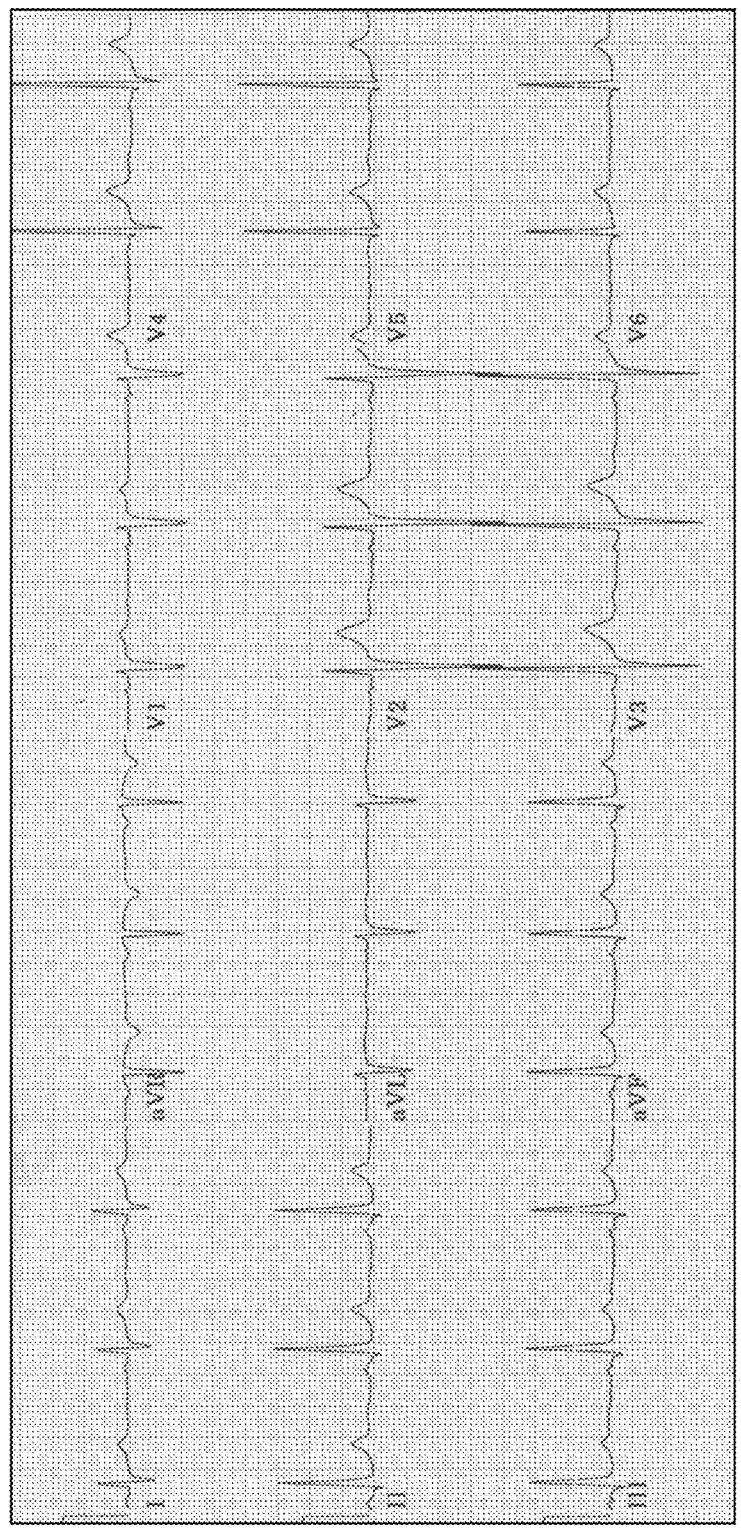
FIG. 1 is an prior art example of a strip chart of electrical signals from a 12-lead EKG monitor connected to a patient with a normal heart.
Figure 2:
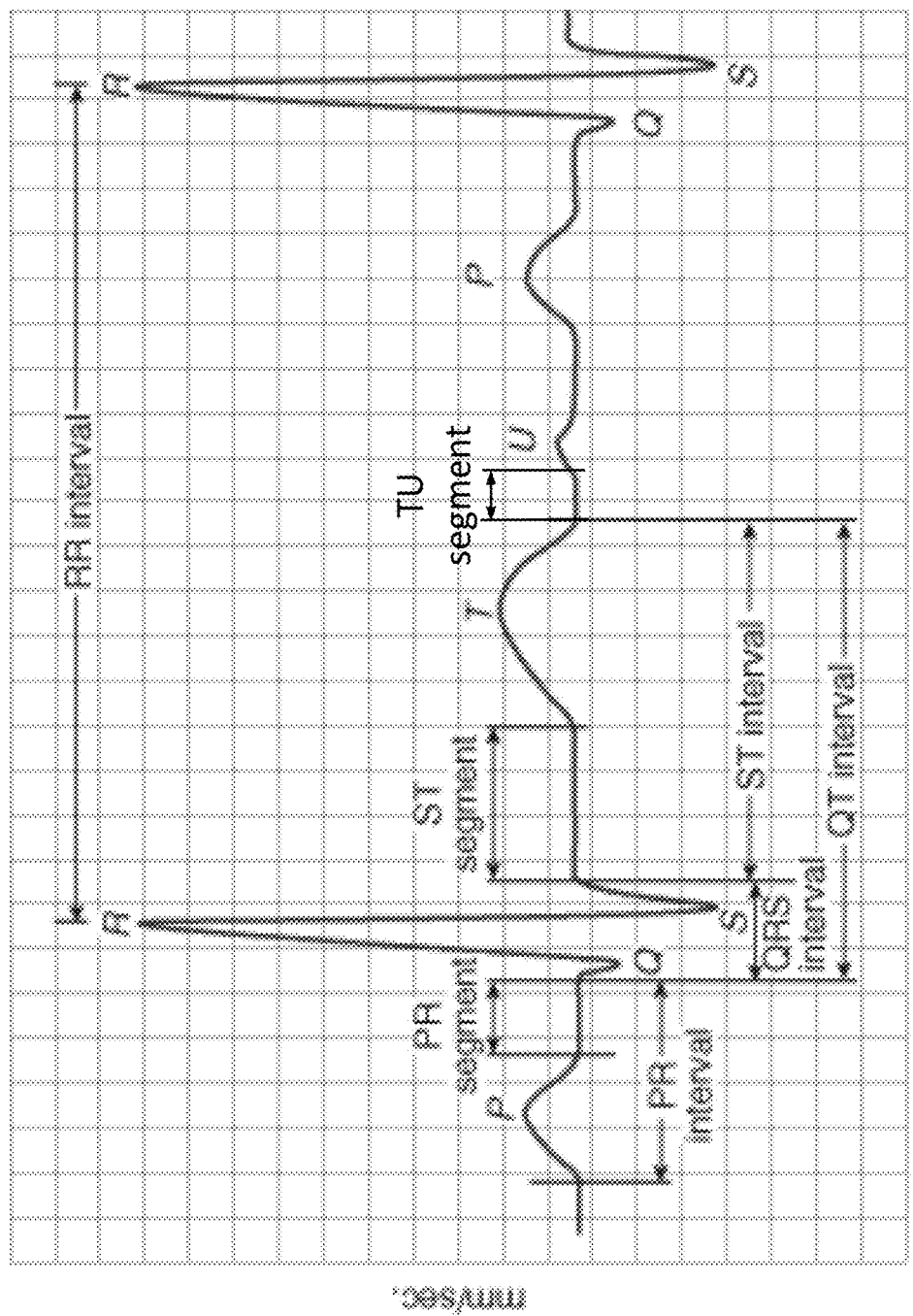
FIG. 2 is a prior art representative plot that identifies the individual waves, intervals and segments that combine to form an EKG wave.
Figure 3:
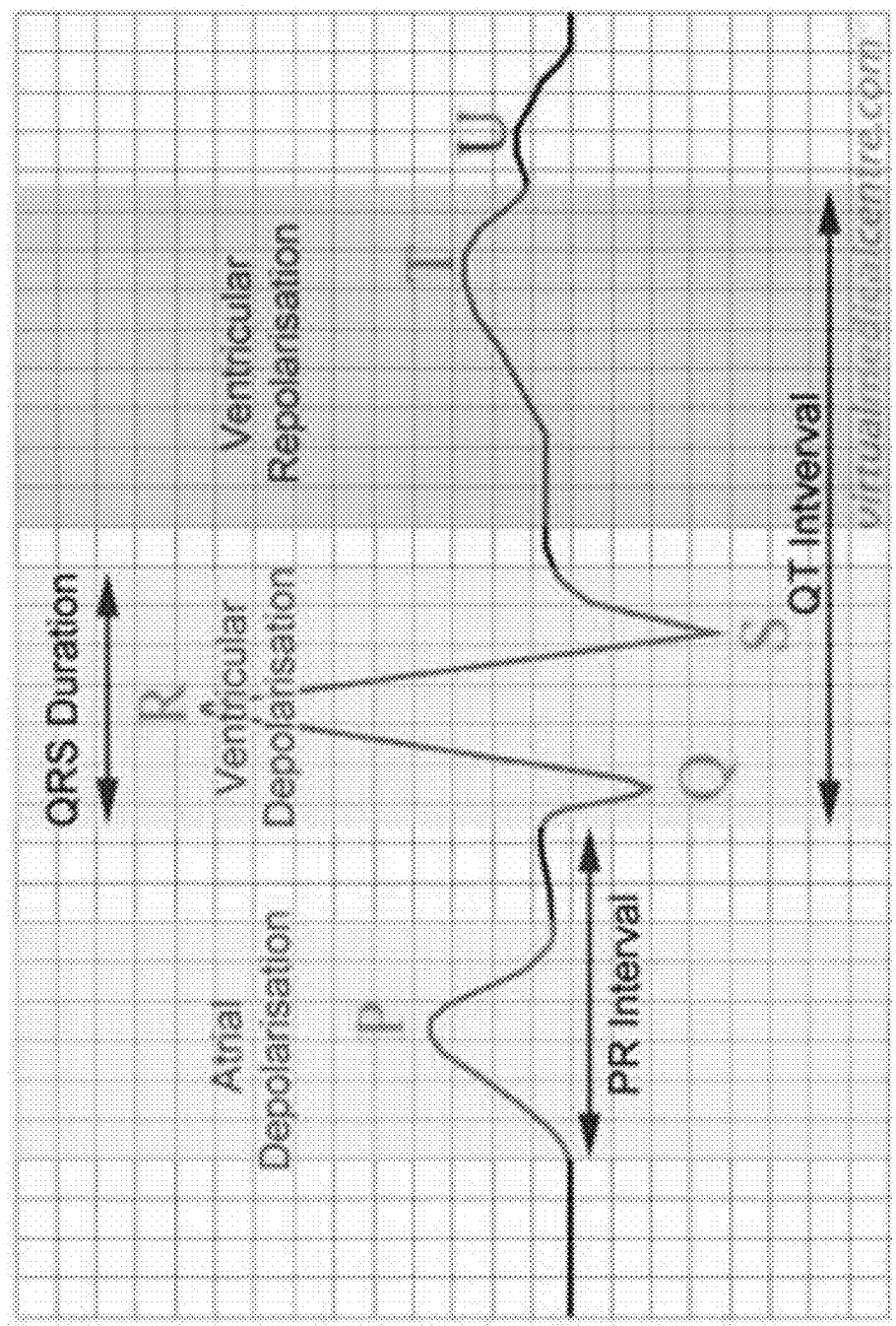
FIG. 3 is a prior art representative plot that identifies the activity of the heart muscles during each phase of a beat.
Figure 4:
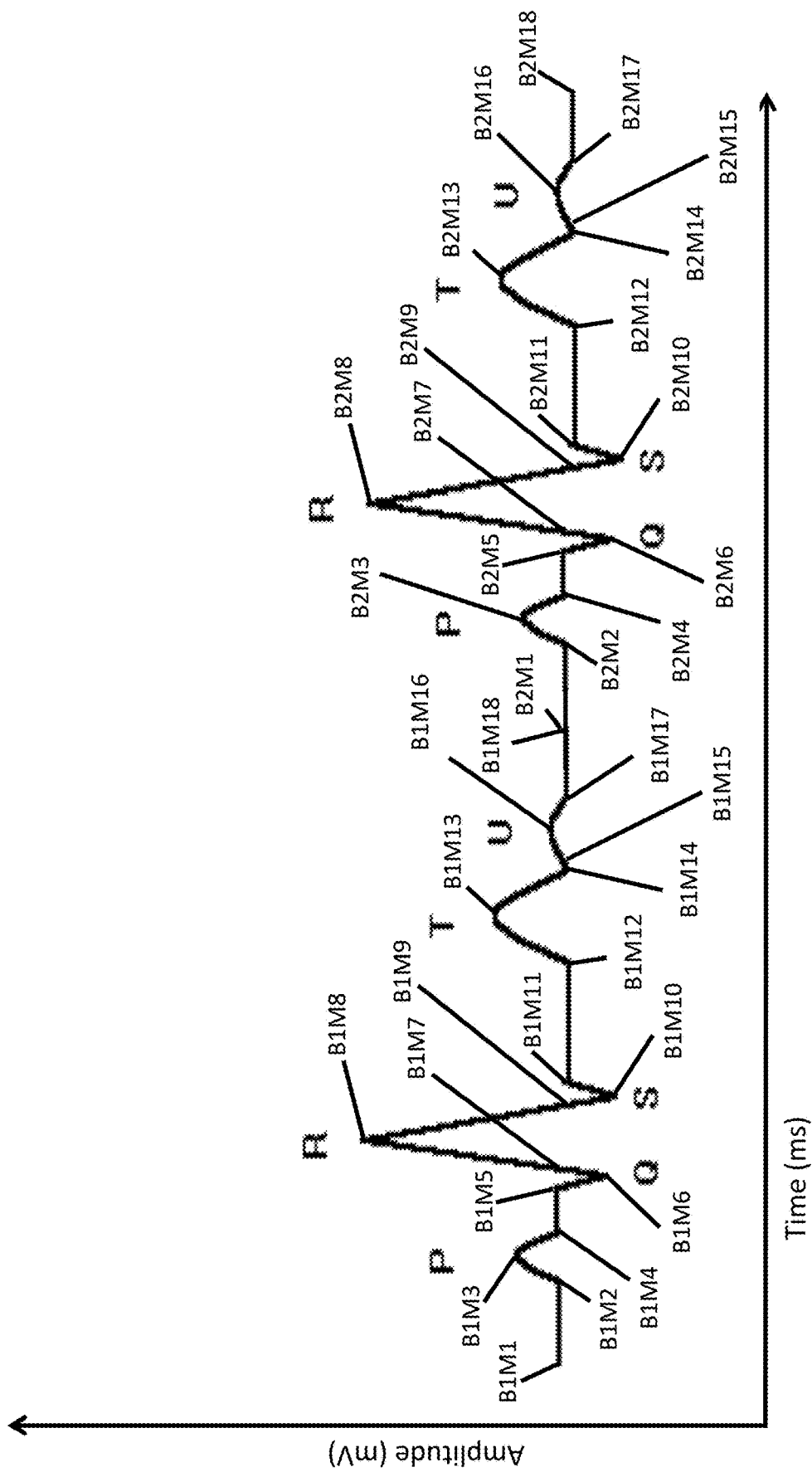
FIG. 4 illustrates an exemplary EKG waveform with transition break points identified.

FIG. 4 illustrates an exemplary EKG waveform showing two beats $B_1$ and $B_2$ with break points $B_1M_1$-$B_1M_{15}$ and $B_2M_1$-$B_2M_{15}$, respectively. The break points $M_1$-$M_{18}$ identify fiducial or transition points of one complete cycle of an EKG waveform.

(Any wave, interval, or segment will be referred to generically herein as a "section.") TABLE I provides an identification of the break points as used in this description.

Although these identifiers may differ from conventional designations, they will be used in this description.

TABLE I

| Break Point | Identifier |
| --- | --- |
| $M_1$ | Beginning of beat |
| $M_2$ | Beginning of P wave ($P_1$) |
| $M_3$ | Peak of P wave ($P_2$) |
| $M_4$ | End of P wave ($P_3$); beginning of PQ/PR interval |
| $M_5$ | Beginning of Q wave ($Q_1$) |
| $M_6$ | Low point of Q wave ($Q_2$) |
| $M_7$ | End of Q wave ($Q_3$); beginning of R wave ($R_1$) |
| $M_8$ | Peak of R wave ($R_2$) |
| $M_9$ | End of R wave ($R_3$); beginning of S wave ($S_1$) |
| $M_{10}$ | Low point of S wave ($S_2$) |
| $M_{11}$ | End of S wave ($S_3$); beginning of ST interval |
| $M_{12}$ | End of ST interval; beginning of T wave ($T_1$) |
| $M_{13}$ | Peak of T wave ($T_2$) |
| $M_{14}$ | End of T wave ($T_3$) |
| $M_{15}$ | Beginning of U wave ($U_1$) |
| $M_{16}$ | Peak of U wave ($U_2$) |
| $M_{17}$ | End of U wave ($U_3$) |
| $M_{18}$ | End of beat |

For example, the sequence $M_2$-$M_4$ identifies the P wave while the sequence $M_5$-$M_{11}$ identifies the QRS complex. Each break point may be defined relative to the previous break point. Thus, an x-value would designate the difference in time (width) from one point to the next and a y-value would designate the positive or negative difference in amplitude. Alternatively, each point may be defined by its absolute x-y coordinates representing time and amplitude, respectively, referenced to the y- and x-axis, respectively.

Either or both of the x and y parameters of a break point may either indicate their absolute values, that is their distance from the y-axis or x-axis, respectively, or may indicate their distance along their respective axis from the previous break point, that is the "delta." As used herein, the term "value" will refer to a delta and the term "coordinate" will refer to an absolute value. However, preferably the x parameter of a break point will be indicated by the x-value (its delta from the previous break point) and the y parameter will be indicated by the y-coordinate (its absolute value from the x-axis).

In order to define a section, it is also necessary to define a path from one break point to the next. The path is identified by an interpolation method i. Some examples of interpolation methods include, but are not limited to, straight line, sinusoidal, square, concave upward, concave downward, notched, among others.

Thus, each break point may be assigned three parameter values x, y, i which together define the location of a break point and the path from the break point to the next break point.

A tools may be provided to allow a user to build a waveform from a sequence of sections. For example, after logging into a web service, a user may be presented with a series of pages, each illustrating a particular section with a selection of varying shapes and widths (in time). For example, one page may allow a user to select a PQ interval by presenting a one-column, nine row table with the rows showing possible PQ intervals from 120 ms to 200 ms in increments of 10 ms. Another page may allow a user to select the overall RR interval by presenting a one-column, seven-row table with the rows showing possible RR intervals from 0.6 l to 1.2 sec. in 0.1 sec. increments. A user may thus make desired selections and construct one or more full heartbeat waveforms. The assembled waveform may then be output as a data file to be loaded into an EKG simulator for research, teaching, testing, and training purposes.

Figure 9A:
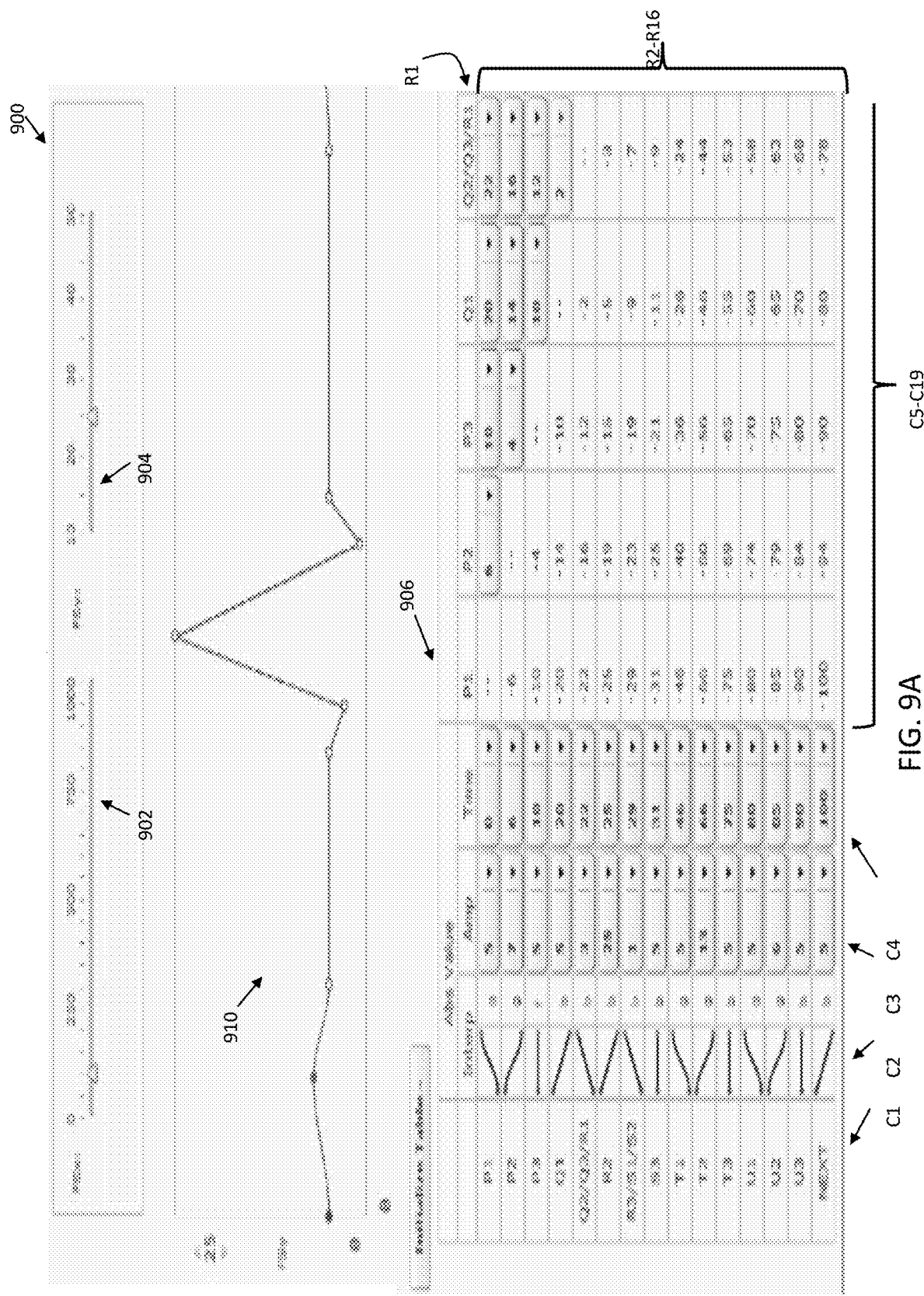
FIGS. 9A and 9B illustrate a screen shot of a display, including a table with drop-down selections and a representation of an EKG waveform constructed from the selections.
Figure 9B:
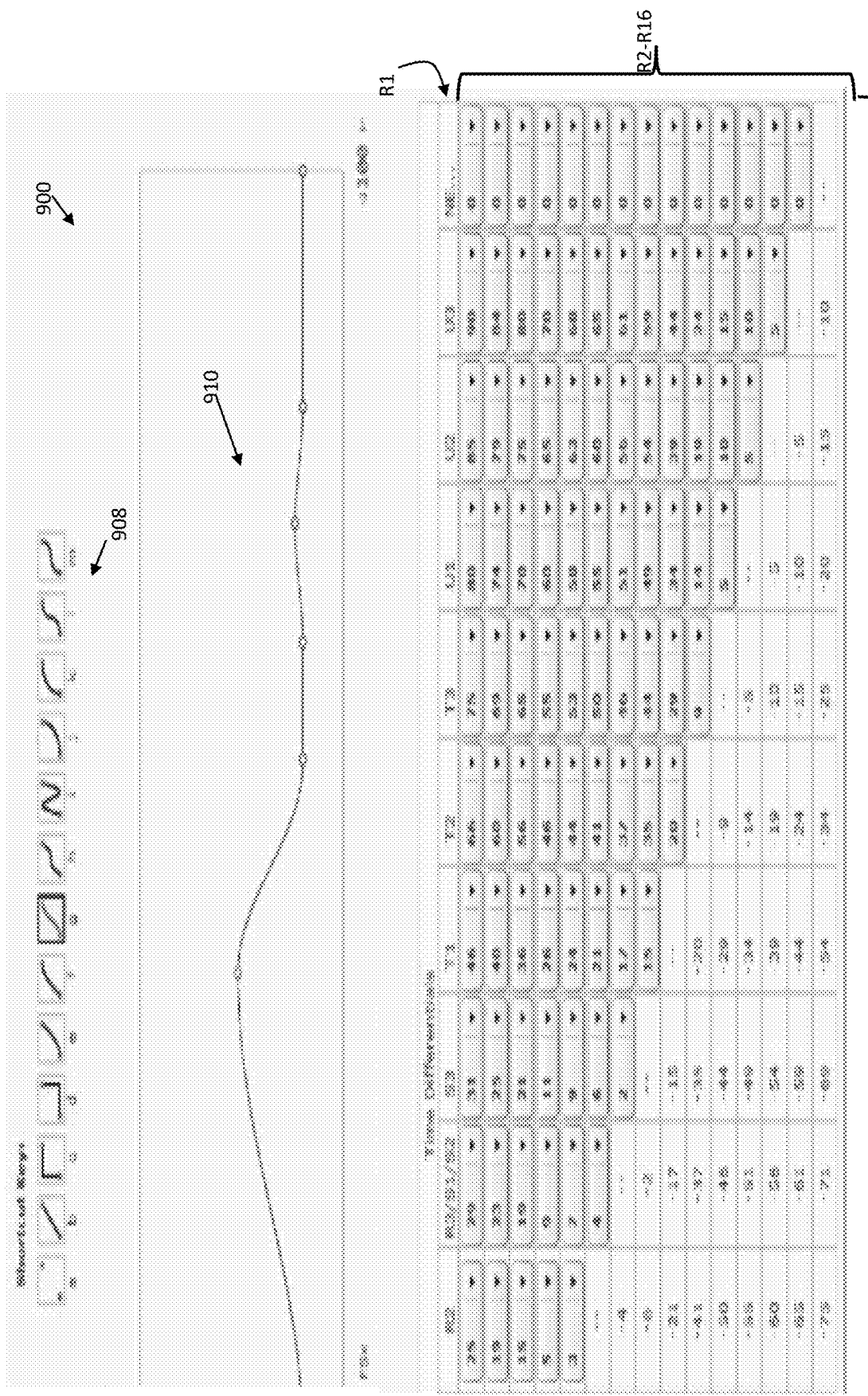

As an alternative to the page-by-page entry method, a user may be presented with a substantially empty table to be filled in with x-values for the break points; that is, time differences from earlier break points. FIG. 5 is an example of a table that may be displayed to the user. The first column and first row identify the break points using the same identification numbers as are used in FIG. 4, $M_1$-$M_{18}$. The second column and second row identify each break point by reference to the wave, interval, or segment in which the break point is located (see TABLE II above). The user may enter a value into each blank cell to designate a time difference between one break point and another. In the table, several cells have been filled in for clarity. For example, to define the total width of the P wave, a value for the time $P_3$-$P_1$ would be entered into the cell at the intersection of column $M_4$ for break point $P_3$ with row $M_2$ for break point $P_1$. Similarly, to define the total width $S_3$-$Q_1$ of the QRS complex, a time value would be entered into the cell at the intersection of column $M_{11}$ for break point $S_3$ with row $M_5$ for break point $Q_3$. The user may fill in as many other cells as desired to specify other time differences. As will be appreciated, the cells at the intersection of break points with themselves have a zero value and the cells that represent negative distances to a previous break point may contain negative values or left blank. In addition, the cells in the row of $M_1$ are unassigned. FIGS. 9A and 9B illustrate completed table 906 and the resulting waveform 910 generated by the values entered into the table cells of rows/columns R2-R16/C5-C19.

An alternative simplified table, illustrated in FIG. 6, may be displayed for the user to enter the x-coordinate (the distance from the y-axis) of each break point, $M_1$-$M_{18}$. It will be understood that the break point labels $M_1$-$M_{18}$ and $P_1$-$U_3$ used in the tables of FIGS. 6-8 are the same labels as are used in the tables of FIGS. 4 and 5. After the user has entered coordinates into each cell and has optionally overridden any default coordinates, the user may change any entry by re-entering a coordinate into a cell. However, the user may be prevented from inputting an invalid entry, such as a coordinate that is less than the coordinate of the preceding break point or greater than the coordinate of the next break point.

Another table, shown in FIG. 7, may be displayed for the user to enter the amplitude of each break point, $M_1$-$M_{18}$. Optionally, a default value may be associated with some or all of the break points. For example, as illustrated in FIG. 7, the break points that identify the beginning and end of sections of a beat may default to an isoelectric line while leaving the break points that identify peaks and valleys of waves to be filled in by the user. The user may override any default amplitude value by replacing it with a desired value.

Further, another table, illustrated in FIG. 8, may be displayed for the user to enter the interpolation method for the path from each break point to the next. Again, certain paths may be assigned a default path. For example, the path from $M_4$/$P_3$ to $M_5$/$Q_1$ (the PQ segment) may default to a zero-slope straight line. The path from $M_7$/$R_1$ to $M_8$/$R_2$ (the first part of the R wave) may default to a straight line whose slope will depend on the amplitude of $M_8$/$R_2$. And, the path from $M_{12}$/$T_1$ to $M_{13}$/$T_2$ (the first part of the T wave) may default to a partial sinusoidal shape whose exact characteristics will depend on the amplitude of the break point $M_{13}$/$T_2$. As with the amplitude entries, the user may override any default path interpolation method by replacing it with a desired method.

Although in some versions the user may enter coordinates and values in a free-form fashion, in other versions the user may be presented with a drop-down list of suggested and valid coordinates or values from which to select.

The tables of FIGS. 7 and 8 are illustrated as separate tables for clarity. In practice, either or both tables may be integrated into the table of FIG. 5 as additional columns and displayed to the user as a single table.

An interactive matrix control/display such as shown in FIGS. 9A and 9B may have many features that help users learn about their measurement and monitoring tools at the same time they enhance their own skills in using and evaluating these tools. The waveform display 910 is scaled using the FSx control 902 and the FSy control 904. The waveform shape is defined by a shape value directly under the waveform display 910. The text string represents the shape value in an x,y,i format. When using the control/display it is not necessary to know how to interpret the shape value, but it is helpful to understand that the displayed waveform is defined by and may be generated from either the shape value or from the shape data in the matrix. In other words, given the shape value, the system can generate the waveform and populate the matrix with data. Vice versa, given the matrix data the system can generate the waveform and the shape value. The matrix contains more data than the shape value, but all the matrix shape data can be derived from the shape value. To generate the waveform, the system needs x,y, and i data for each breakpoint, 14 in this case. If three independent break points were defined for each of the six fiducial points (PQRSTU), 18 points would be required, but in this case fiducial points Q2/Q3/R1 share one point and R3/S1/S2 share one point. So only fourteen breakpoints are required for eighteen fiducial points. Sixteen break points are identified for the waveform shown in FIG. 4 because Q2 and S2 each have their own break point leaving only Q3/R1 to share one point and R3/S1 to share another.

FIGS. 9A and 9B illustrate a screen shot of an interactive control/display 900 that may be presented to a user to construct an EKG or other waveform. Using a touch screen, mouse, or other input device, the user may select a range of values for the x-axis 902 and for the y-axis 904. The lower portion of the display 900 presents a matrix 906 of one variation of the table of FIG. 5 with elements of FIGS. 7 and 8 and other features integrated into it. The first row R1 and first column C1 identify the three break points of each wave P, Q, R, S, T, and U. Because some break points corresponding to fiducial points typically coincide with other break points with no change in x and y coordinates, they are not shown separately. The cells in the second column C2 allow the user to select an interpolation method i, such as from a list or icon display 908. The cells in the third and fourth columns C3, C4 allow the user to select, such as from drop-down lists, the absolute amplitude (along the y-axis) and the absolute time (along the x-axis), respectively, of each break point. The cells at the intersections of the remainder of the rows R2-R16 and columns C4-C18 provide drop-down lists that allow the user to select values that represent the time differential between the break point identified in column C1 and the break point identified in row R1. Cells at the intersection of break points with themselves represent a zero distance and may be left blank or contain symbols such as dashes that are believed to be more useful than zeros. Negative values are shown in the lower half of the matrix. Thus, for each break point, the user may either enter an x-coordinate (the absolute time along the x-axis) in column C2 or enter an x-value (difference from the previous break point) in an appropriate cell in the main body of the matrix 906.

In addition, the user may select an interpolation method from a set of icons 908 to define a path from one break point to the next, and preferably a column C2 may be inserted to identify the iValue selected for each break point.

Displayed between the x, y, and i selections 902, 904, 908 and the matrix 906 is a complete graphical representation of a waveform, in this case a heart beat, from the first break point to the last. Thus, the user is able to see the creation of the waveform progress as entries are input into the cells of the matrix. The user is further able to change any entry in real time and immediately see the effect on the chart. In one embodiment (not shown), the break points displayed in the waveform representation are aligned with their respective columns in the matrix below.

The display of the waveform representation may be interactive whereby the user may use an input device to "grab" and move break points to new locations in the x or y directions directly on the chart.

After the user has entered desired information, the waveform may be assembled digitally and then output as a data file. The data file may be loaded into an EKG simulator to simulate a patient's heart for testing or training purposes.

Figure 10:
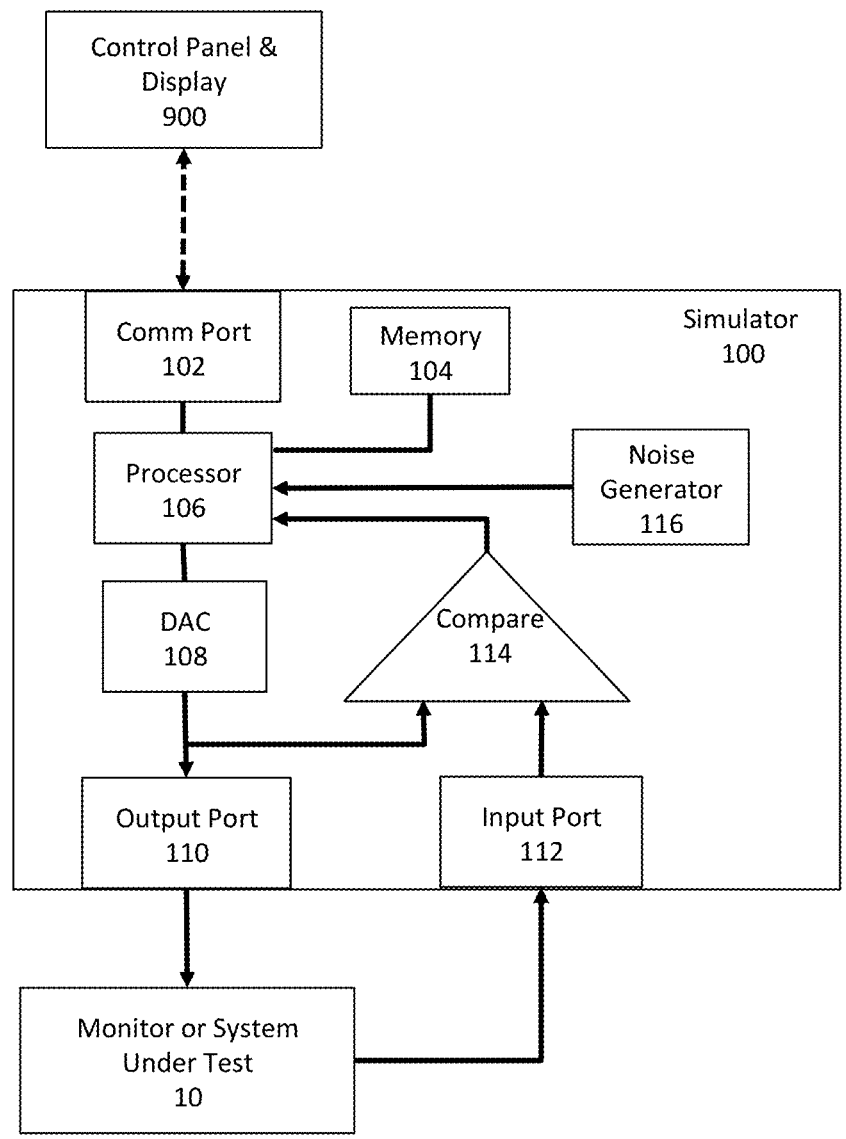
FIG. 10 is a block diagram of an embodiment of a EKG simulator of the present invention.

FIG. 10 is a block diagram of an embodiment of a signal simulator 100 of the present invention. The simulator 100 is coupled to the control and display panel 900 and is configured to output signals to a system under test (SUT) 10, such as an EKG or other biological signal monitor. The panel 900 and simulator 100 may be coupled through a wired connection or, preferably, through a wireless connection, such as WiFi or Bluetooth® enabled. In such a configuration, the panel 900 may thus be used remotely.

The simulator 100 may include a communication (comm) port 102 configured to receive programming signals from the panel 900, a memory 104 configured to store instructions and predetermined values, a processor 106 configured to process the programming and predetermined values according to the instructions stored in the memory, a digital-to-analog converter (DAC) 108 configured to convert the processed values into analog output signals, and an output port 110 configured to make the analog output signals available to the SUT 10. The simulator 100 may also include an input port 112 to receive signals from the SUT 10 and a comparator 114 configured to compare the signals 114A from the SUT 10 against the signals 114B from the DAC 108. A comparison of the signals, such as in graphical form, may then be displayed on the panel 900. Although the input port 112 and the comparator 114 are shown in FIG. 10 as being digital components, they may instead be analog components, in which case the input signals 114B would be received directly from the processor 106 without conversion.

The panel 900 may be part of any appropriate input and display product, such as a computer, tablet computer, or smart phone, to receive programming values from a user, output programming signals to the simulator 100, and receive signals for display from the simulator 100.

The simulator 100 may transmit simulated physiological electrical (biological process) signals to the monitor SUT 10 in place of signals from patient electrodes for the purpose of testing or verifying various functions of the monitor. When the SUT 10 is an EKG monitor, such functions may include those related to variations in heart rate. As noted above, the comparator 114 is configured to compare the signals from the SUT 10 against the signals from the DAC 108 and a comparison of the signals may then be displayed on the panel 900. In this manner, the performance of the SUT 10 may be verified and adjustments may be made as required, such as if the two signals are misaligned.

The simulator 100 may also be programmed to identify when the differential between two break points falls outside of a predetermined range, thus indicating the possibility of an abnormality. For example, when the simulator 100 is coupled to an EKG monitor (SUT 10), it may measure the time between the $T_3$ break point to the next $R_2$ break point. If time is less than about 260 ms, a heart irregularity may be indicated and the simulator 100 may provide an appropriate warning signal to the user.

The raw signal that is received by an EKG monitor is not "pure" in that the electrodes also pick up unrelated electrical activity, circuitry noise, and other artifacts, all collectively referred to herein as noise. An EKG monitor includes circuitry to filter out the noise so that the wave form that is displayed is relatively clean. The simulator 100 may also include a noise generator 116 and be programmed to inject or mix noise into a user-created EKG wave form to more accurately simulate the signals from an actual patient's heart. The mixed signal is transmitted to the monitor or SUT 10 through the output port 110, fed back to the simulator 100 through the input port 112, and compared 114 to the transmitted signal. In this manner, the capability of the monitor or SUT 10 to filter the noise and leave only the useful information may be assessed.

The simulator 100 may provide an additional training benefit by allowing users to generate custom designed EKG waveforms for study, instead of having to find and study actual EKG patient charts that may be unclear, inconsistent, noisy, or contain various artifacts.

Figure 11:
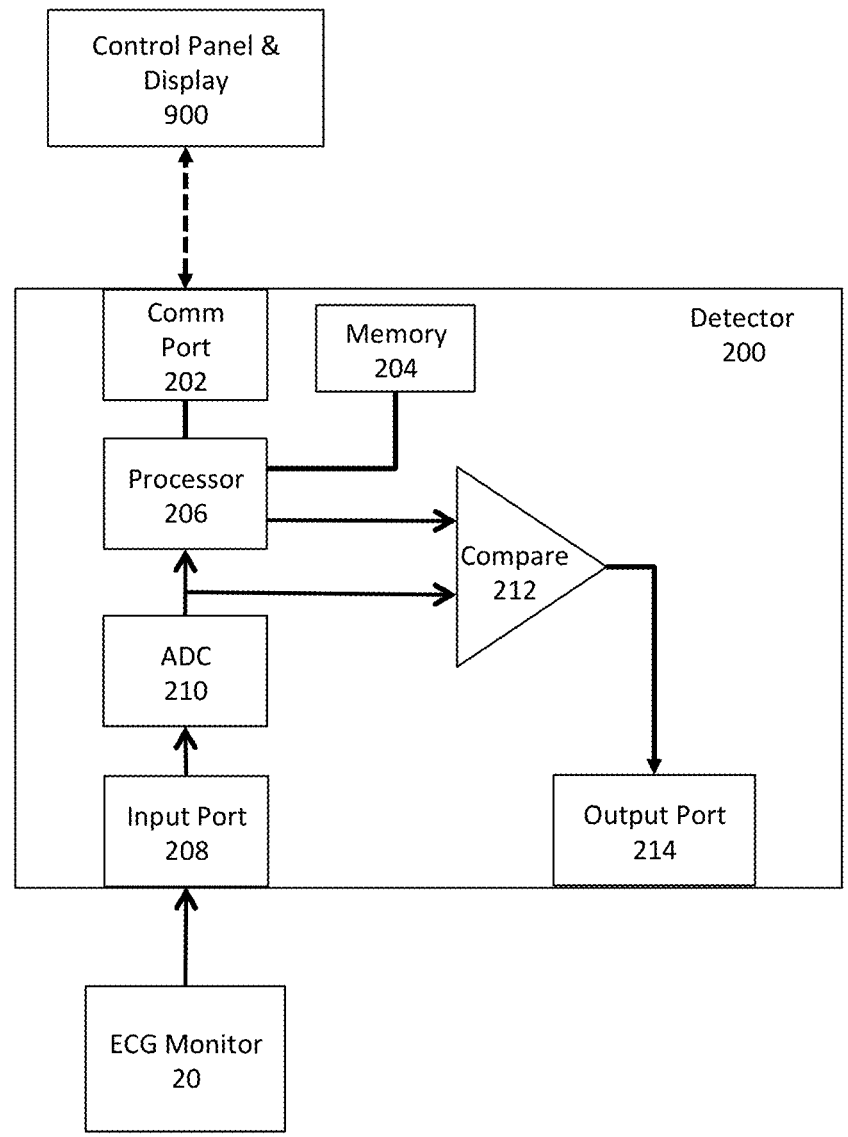
FIG. 11 is a block diagram of an embodiment of a detector of the present invention.

An embodiment of the present invention includes a method and system to isolate and display the Ta wave, which represents atrial repolarization and which is typically not visible on an EKG. FIG. 11 is a block diagram of an embodiment of such a detector 200. The detector 200 includes a comm port 202 through which the control panel and display 900 may communicate with the detector 200. The detector 200 also includes a memory 204 configured to store instructions and a processor 206 configured to process the programming according to the instructions stored in the memory 204 The detector 200 also includes an input port 208 configured to receive analog signals from an EKG monitor and an analog-to-digital converter (ADC) 210 configured to convert the received signals into digital signals to make the digital signals available to the processor 206. It will be appreciated that the EKG monitor 20 may have a digital output in which case the ADC 210 is unnecessary and the signal from the input port 208 may be sent directly to the processor 206.

Instructions stored in the memory 204 and executed by the processor 206 cause the processor 206 to receive a full EKG waveform from the EKG monitor and estimate the portion of the EKG waveform that represents ventricular depolarization and repolarization. Further instructions cause the processor 206 to send the estimated ventricular waveforms as one input to a comparator 212. A second input to the comparator 212 receives the full EKG from the ADC 210 (or directly from the input port 208). The comparator 212 subtracts the estimated ventricular waveforms from the full EKG waveform and outputs the result to an output port 214 for display or printing and analysis. The output result represents atrial depolarization (PR Interval) and estimated atrial repolarization (Ta wave).

Determination of estimated ventricular depolarization may be made in a number of ways. The processor may be programmed to identify the appropriate break points. Referring to TABLE II above and FIG. 4, these break points include: $Q_1(M_5)$, $Q_2(M_6)$, $Q_3/R_1(M_7)$, $R_2(M_8)$, $R_3/S_1(M_9)$, $S_2(M_{10})$, $S_3(M_{11})$, $T_1(M_{12})$, $T_2(M_{13})$, and $T_3(M_{14})$. Alternatively, a user of the system 200 may manually enter the breakpoints through the control panel and display 900 as described above.

It is believed that the estimated ventricular depolarization may also be determined through frequency or Fourier analysis. The inventor believes that ventricular depolarization results in electrical signals that are at a higher frequency than electrical signals from atrial repolarization. Consequently, the processor 206 may be programmed with instructions to send to the comparator 212 that portion of the selected selection of the EKG signal having frequency components above a predetermined level, representing ventricular depolarization. After the comparator 212 subtracts this portion of the full EKG signal, the output result represents an estimated representation of the atrial repolarization. Alternatively, the processor 206 may be programmed with instructions to determine that portion of the full EKG signal having a frequency below a predetermined level and directly output a representation of atrial activity.

The inventor also believes that the Q and S waves may be affected by the Ta wave. Thus, in another embodiment, instructions stored in the memory 204 and executed by the processor 206 again cause the processor 206 to receive a full EKG waveform and to estimate ventricular depolarization. Further instructions cause the processor 206 to send the estimated wave as one input to the comparator 212. A second input to the comparator 212 receives the full EKG from the ADC 210 (or directly from the input port 208). The comparator 212 subtracts the estimated wave from the full EKG waveform and outputs the result to the output port 214 for display or printing and analysis. The output result may then represent an EKG waveform with estimated atrial repolarization instead of a composite signal including both atrial and ventricular activity.

Figure 12:
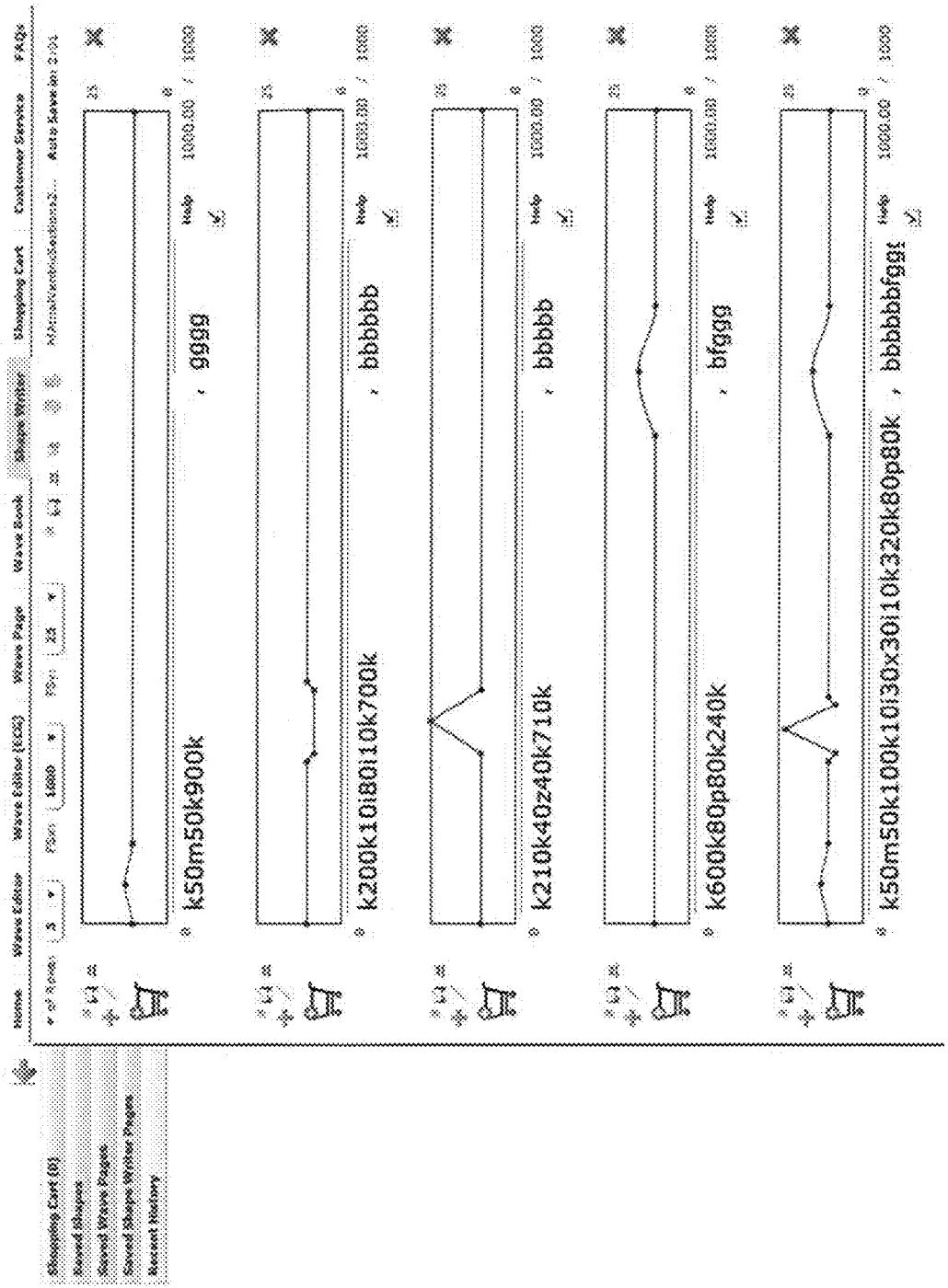
FIG. 12 illustrates a screen shot of a display of the construction of an EKG waveform generated by summing representations of an atrial depolarization wave, an estimated atrial repolarization wave, a ventricular depolarization wave, and a ventricular repolarization wave.

As with the previous embodiment, determination of ventricular depolarization may be made in a number of ways, including programming the processor with the appropriate break points ($R_1(M_7)$, $R_2(M_8)$, and $R_3(M_9)$) or entering the break points manually. An example of such programming is illustrated in FIG. 12, which is a screen shot of a display of the construction of an EKG waveform. The full waveform, shown in the bottom plot, is generated by summing representations of an atrial depolarization wave (top plot), an estimated atrial repolarization wave (second plot), a ventricular depolarization wave (third plot), and a ventricular repolarization wave (fourth plot).

Sources for information used to estimate repolarization and depolarization for atrial and ventricular activity include the following: EKG Data Bases, various electrode lead configurations, frequency content of portions of fiducial waveforms, expert opinions, intra-cardiac and catheter electrodes, missing beats, what-if scenarios, trial and error comparisons, comparison of normal beats with otherwise normal without atrial activity, otherwise normal beats without ventricular activity, statistical methods including Bayes conditional probability techniques to improve estimates based on prior estimates, methods used for identifying musical instruments, and other sources of sound and electrical activity.

With respect to a method of estimating hidden information or wave in a composite waveform, the section of a waveform in which the hidden wave is expected to be found (search section SS) is identified by defining a start point and a stop point on the x-axis. The SS wave may include many components, but for simplicity just two components are relevant: a dominant wave P1 and a hidden wave P2. Any other components that may be in the composite wave are treated as not being significant for purposes of estimating the hidden wave. These other components are assumed to be included in either P1, P2, or overlapping both. When defining P1, the intent is to define a wave that is less complex than SS but still believed to not affect the analysis leading to an interpretation or reading of the composite waveform.

For example, a reading of an EKG generally indicates whether the waveform is normal or not normal with clarifying additional remarks and commonly d'esn't consider atrial repolarization (the Ta wave or repA). When trying to isolate a wave that represents the usually hidden wave repA, a plausible section SS of the full EKG waveform in which to search would contain waves believed to include the hidden wave and ventricular depolarization (the QRS complex or depV). In this case, the SS is the composite wave which has two components, repA and depV. A simplified version of the dominant wave depV is defined as P1 with the understanding that SS=P1+P2. P2 may then be calculated as P2=-SS -P1. For an EKG, reading this corresponds to repA =-SS -depV, where P1=depV and P2=repA. Now a decision is made about whether depV has been defined in a way to provide an SS that is a plausible representation of the waveform used by the analysis process to provide the reading. When adding or subtracting component parts of a composite waveform, it is assumed that each component has the same number of samples as the composite waveform as illustrated in FIG. 12. For simplicity, it also helps to consider that the isoelectric line has zero amplitude and that sample amplitudes have positive and negative amplitudes around it.

Figure 13:
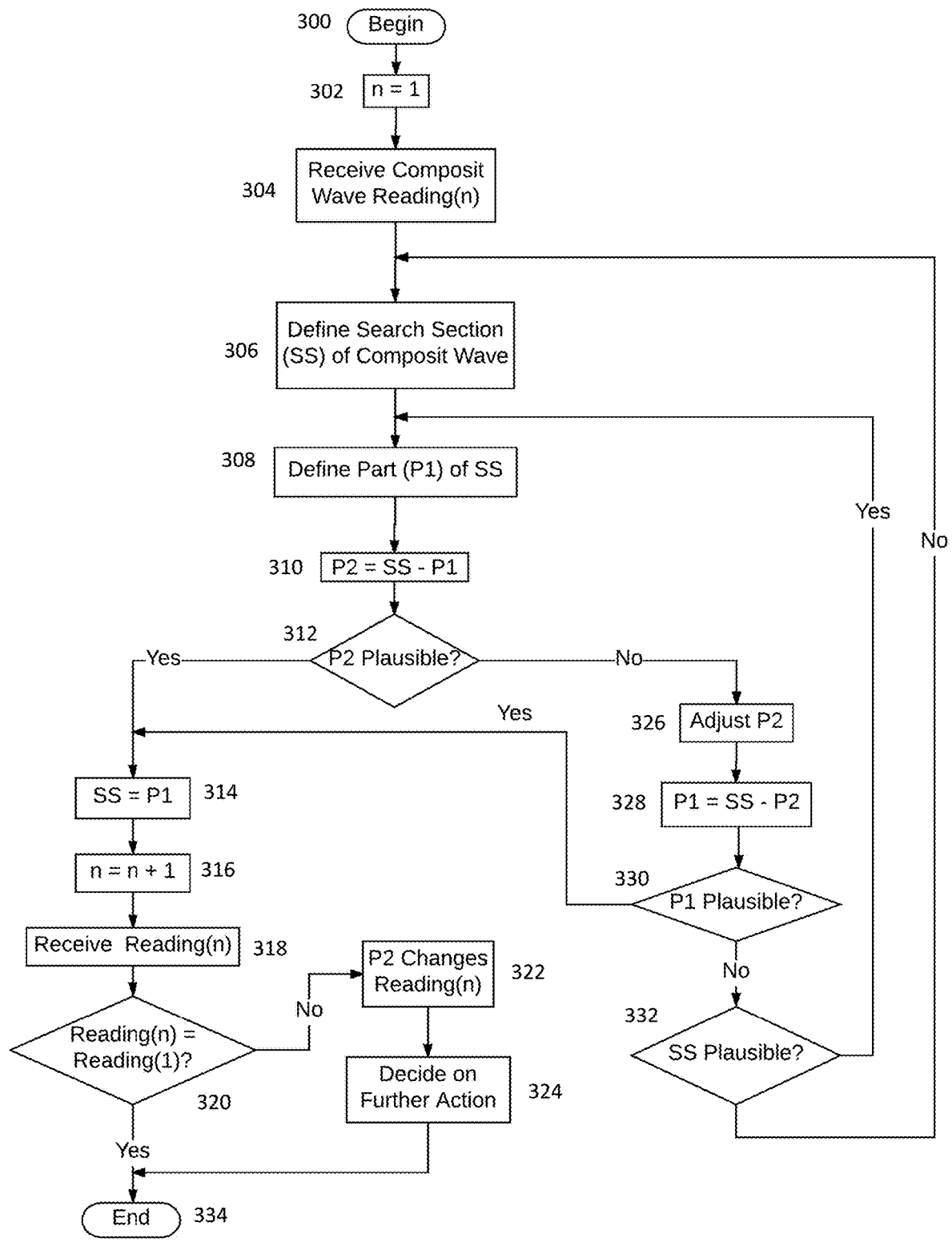
FIG. 13 is a flowchart of an embodiment of a method of using the system of FIG. 10.

More specifically referring to the flowchart of FIG. 13, an embodiment of a step by step method of using the system is as follows:
- 300. Begin.
- 302. Set n=1.
- 304. Receive a composite wave signal with an interpretation called Reading(n) that describes support and diagnosis without performing an isolation process.
- 306. Define a Search Section (SS) within the composite signal that includes a waveform having characteristics believed to be essential based on current conditions to support the reading.
- 308. Define Part 1 (P1) of SS where P1 is estimated to be substantially less complicated than SS but still supports the Reading.
- 310. Set Part 2 (P2)=SS−P1.
- 312. If P2 is not plausible, go to Step 326, otherwise continue.
- 314. Set SS=P1.
- 316. Set n=n+1.
- 318. Receive Reading (n).
- 320. If Reading(n) equals Reading(1), P2 has no significant effect on Reading(1) and go to Step 334, otherwise continue.
- 322. P2 changes Reading(n).
- 324. Decide on further action and go to Step 334.
- 326. Adjust P2.
- 328. Set P1=SS−P2.
- 330. If P1 is plausible, go to Step 314, otherwise continue.
- 332. If SS is plausible, go to Step 308, otherwise go to Step 306.
- 334. End.

This step by step method is an iterative process that may help users decide whether waveform isolation helps improve their interpretations and to collect data for future applications.

The description of the present invention has been presented for purposes of illustration and description, but is not intended to be exhaustive or limited to the invention in the form disclosed. Many modifications and variations will be apparent to those of ordinary skill in the art. The embodiments were chosen and described in order to best explain the principles of the invention, the practical application, and to enable others of ordinary skill in the art to understand the invention for various embodiments with various modifications as are suited to the particular use contemplated.

What is claimed is:

1. A system for estimating a signal hidden within a composite electrical signal, the system comprising:
   - an input for receiving an electrical signal and a first reading, the electrical signal comprising a search section SS comprising the sum of a first signal P1 and a hidden second signal P2 and the first reading describing an initial evaluation of the electrical signal based upon an assumption that SS equals P1 without regard to the hidden signal P2;
   - a processor coupled to the input; and
   - a memory configured to store instructions executable by the processor to cause the processor to:
     - estimate the hidden signal P2; and
     - calculate a new signal P1 from which a second reading is provided, the second reading describing an updated evaluation of the electrical signal based upon subtracting the estimated hidden signal P2 from the search section SS;
   - whereby, if the second reading is different from the first reading, the effect of the estimated hidden signal P2 is considered before taking action based on the first and second readings.

2. The system of claim 1, wherein:
   - the composite electrical signal is an EKG signal;
   - the first signal P1 comprises a portion of the EKG signal representing a ventricular depolarization wave depV;
   - the hidden signal P2 comprises a portion of the EKG signal representing an atrial repolarization wave repA; and
   - the search section SS comprises a section of the EKG signal believed to include the ventricular depolarization wave depV and the atrial repolarization wave repA;
   - whereby, the processor estimates depV and repA from the relations SS=depV+repA.

3. The system of claim 1, comprising further instructions causing the processor to determine whether the signals P1 and P2 are plausible.

4. The system of claim 3, comprising further instructions causing the processor to alternately change signal P1 and signal P2 until both are plausible based on SS=P1+P2.

5. The system of claim 3, comprising further instructions causing the processor to determine whether the search section SS is plausible.

6. A method for estimating a signal hidden within a composite electrical signal, the method comprising:
   - receiving a composite electrical signal and a first reading, the composite electrical signal comprising a search section SS comprising the sum of a first signal P1 and a hidden second signal P2 and the first reading describing an initial evaluation of the composite electrical signal based upon an assumption that SS equals P1 without regard to the hidden signal P2; and estimating the hidden signal P2;

calculating a new signal P1 from which a second reading is provided, the second reading describing an updated evaluation of the composite electrical signal based upon subtracting the estimated hidden signal P2 from the search section SS; and if the second reading is different from the first reading, considering the effect of the estimated hidden signal P2 before taking action based on the first and second readings.

7. The method of claim 6, wherein:

the composite electrical signal is an EKG signal;

the first signal P1 comprises a portion of the EKG signal representing a ventricular depolarization wave depV;

the hidden signal P2 comprises a portion of the EKG signal representing an atrial repolarization wave repA; and the search section SS comprises a section of the EKG signal believed to include the ventricular depolarization wave depV and the atrial repolarization wave repA; and estimating depV and repA from the relation SS=depV+repA.

8. The method of claim 6, further comprising determining whether the signals P1 and P2 are plausible.

9. The method of claim 8, further comprising alternately changing signals P1 and P2 until both are plausible based on SS=P1+P2.

10. The method of claim 8, further comprising determining whether the search section SS is plausible.

\* \* \* \* \*